(12) United States Patent
Kolodney et al.

(10) Patent No.: US 7,622,130 B2
(45) Date of Patent: *Nov. 24, 2009

(54) METHODS AND COMPOSITIONS FOR THE NON-SURGICAL REMOVAL OF FAT

(75) Inventors: Michael S. Kolodney, Santa Monica, CA (US); Adam M. Rotunda, Los Angeles, CA (US)

(73) Assignees: Los Angeles Biomedical Research Institute at Harbor UCLA-Medical Center, Torrance, CA (US); The Regents of the University of California, Oakland, CA (US)

( * ) Notice: Subject to any disclaimer, the term of this patent is extended or adjusted under 35 U.S.C. 154(b) by 958 days.

This patent is subject to a terminal disclaimer.

(21) Appl. No.: 11/054,171

(22) Filed: Feb. 8, 2005

(65) Prior Publication Data

US 2005/0261258 A1 Nov. 24, 2005

Related U.S. Application Data

(60) Provisional application No. 60/572,879, filed on May 19, 2004.

(51) Int. Cl.
*A61K 8/02* (2006.01)
(52) U.S. Cl. .................................................. 424/401
(58) Field of Classification Search ................. 424/401
See application file for complete search history.

(56) References Cited

U.S. PATENT DOCUMENTS

| | | | |
|---|---|---|---|
| 4,113,882 A | 9/1978 | Okazaki et al. |
| 4,117,121 A | 9/1978 | Gallo-Torres et al. |
| 4,158,707 A | 6/1979 | Steffen et al. |
| 4,664,910 A | 5/1987 | Caserio et al. |
| 4,681,876 A | 7/1987 | Marples et al. |
| 4,851,435 A | 7/1989 | Sauer et al. |
| 4,866,044 A | 9/1989 | Sato et al. |
| 4,994,439 A | 2/1991 | Longenecker et al. |
| 5,085,864 A | 2/1992 | Cannon et al. |
| 5,288,498 A | 2/1994 | Stanley et al. |
| 5,326,562 A | 7/1994 | Scott |
| 5,344,822 A | 9/1994 | Levine et al. |
| 5,371,104 A | 12/1994 | Feigenbaum et al. |
| 5,395,545 A | 3/1995 | Fischer et al. |
| 5,506,218 A | 4/1996 | Parker et al. |
| 5,616,342 A | 4/1997 | Lyons |
| 5,674,855 A | 10/1997 | Levine et al. |
| 5,759,445 A | 6/1998 | Yamamoto et al. |
| 5,863,554 A | 1/1999 | Illum |
| 5,876,721 A | 3/1999 | Alexander et al. |
| 5,891,083 A | 4/1999 | Capella et al. |
| 5,942,248 A | 8/1999 | Barnwell |
| 5,952,392 A | 9/1999 | Katz et al. |
| 6,120,805 A | 9/2000 | Spenlehauer et al. |
| 6,197,327 B1 | 3/2001 | Harrison et al. |
| 6,221,378 B1 | 4/2001 | Modi |
| 6,225,343 B1 | 5/2001 | Behl et al. |
| 6,251,428 B1 | 6/2001 | Yoo |
| 6,255,502 B1 | 7/2001 | Penkler et al. |
| 6,294,192 B1 | 9/2001 | Patel et al. |
| 6,315,984 B1 | 11/2001 | Modi |
| 6,350,458 B1 | 2/2002 | Modi |
| 6,375,975 B1 | 4/2002 | Modi |
| 6,383,471 B1 | 5/2002 | Chen et al. |
| 6,416,779 B1 | 7/2002 | D'Augustine et al. |
| 6,417,179 B1 | 7/2002 | Burkhart et al. |
| 6,451,286 B1 | 9/2002 | Modi |
| 6,489,312 B1 * | 12/2002 | Stogniew et al. ............ 514/109 |
| 6,537,561 B1 | 3/2003 | Fukui et al. |
| 6,663,885 B1 | 12/2003 | Hager et al. |
| 6,713,470 B2 | 3/2004 | Jackson |
| 6,849,263 B2 | 2/2005 | Modi |
| 6,884,768 B2 | 4/2005 | Kimura et al. |
| 2002/0031558 A1 | 3/2002 | Yoo |
| 2002/0058010 A1 | 5/2002 | Picard-Lesboureyries et al. |
| 2002/0107291 A1 | 8/2002 | De Tommaso |
| 2002/0168402 A1 | 11/2002 | Kipp et al. |
| 2003/0027833 A1 | 2/2003 | Cleary et al. |
| 2003/0035831 A1 | 2/2003 | Modi |
| 2003/0054981 A1 | 3/2003 | Milton et al. |

(Continued)

FOREIGN PATENT DOCUMENTS

| | | |
|---|---|---|
| CA | 2033725 | 5/2001 |
| EP | 0426029 A1 | 5/1991 |
| EP | 0439042 B1 | 6/1995 |
| EP | 0439513 B1 | 3/1996 |
| EP | 0730860 B1 | 1/2002 |

(Continued)

OTHER PUBLICATIONS

Ablon G, Rotunda AM. Treatment of lower eyelid fat pads using phosphatidylcholine: clinical trial and review. Derm Surgery 2004, 30:422-7.

Alkan-Onyuksel H, Ramakrishnan S, Chai HB, Pezzuto JM. A mixed micellar formulation suitable for the parenteral administration of taxol. Pharm Res 1994, 11:206-12.

Almgren M. Mixed micelles and other structures in the solubilization of bilayer lipid membranes by surfactants. Biochim Biophys Acta 2000, 1508:146-63.

(Continued)

*Primary Examiner*—Yong S Chong

(57) ABSTRACT

Compositions and methods useful in the non-surgical removal of localized fat deposits in patients in need thereof using pharmacologically active detergents are disclosed. The pharmacologically active detergent compositions can additionally include anti-inflammatory agents, analgesics, dispersion agents and pharmaceutically acceptable excipients but do not contain phosphotidylcholine. The pharmacologically active detergent compositions are useful for treating localized accumulations of fat including lower eyelid fat herniation, lipodystrophy and fat deposits associated with cellulite and do not require surgical procedures such as liposuction.

2 Claims, 6 Drawing Sheets

U.S. PATENT DOCUMENTS

| | | |
|---|---|---|
| 2003/0064097 A1 | 4/2003 | Patel et al. |
| 2003/0072807 A1 | 4/2003 | Wong et al. |
| 2003/0077329 A1 | 4/2003 | Kipp et al. |
| 2003/0161886 A1 | 8/2003 | Dickinson et al. |
| 2003/0186933 A1 | 10/2003 | Yoo |
| 2003/0219472 A1 | 11/2003 | Pauletti et al. |
| 2004/0022862 A1 | 2/2004 | Kipp et al. |
| 2004/0038952 A1 | 2/2004 | Feher |
| 2004/0067919 A1 | 4/2004 | Jee |
| 2004/0096494 A1 | 5/2004 | Siekmann et al. |
| 2004/0101569 A1 | 5/2004 | Rang |
| 2004/0115255 A1 | 6/2004 | Leigh et al. |
| 2004/0141949 A1 | 7/2004 | Rosenthal et al. |
| 2004/0161407 A1 | 8/2004 | Kimura et al. |
| 2004/0201117 A1 | 10/2004 | Anderson |
| 2004/0213855 A1 | 10/2004 | Pettersson et al. |
| 2004/0220283 A1 | 11/2004 | Zhang et al. |
| 2005/0019404 A1 | 1/2005 | Sung et al. |
| 2005/0079228 A1 | 4/2005 | Jaiswal et al. |
| 2005/0089555 A1 | 4/2005 | Boderke et al. |
| 2005/0123582 A1 | 6/2005 | Sung et al. |
| 2005/0143347 A1 | 6/2005 | Boderke et al. |
| 2005/0158408 A1 | 7/2005 | Yoo |
| 2005/0163821 A1 | 7/2005 | Sung et al. |
| 2005/0266065 A1 | 12/2005 | Perrier et al. |
| 2005/0287199 A1 | 12/2005 | Denney et al. |
| 2006/0074057 A1 | 4/2006 | Marchewitz |
| 2006/0222673 A1 | 10/2006 | Chern et al. |
| 2006/0222695 A1 | 10/2006 | Zadini et al. |

FOREIGN PATENT DOCUMENTS

| | | |
|---|---|---|
| EP | 0806940 B1 | 4/2003 |
| EP | 1005324 B1 | 3/2005 |
| JP | 03 048622 | 3/1991 |
| WO | WO 90/12583 | 11/1990 |
| WO | WO 94/04177 | 3/1994 |
| WO | WO 02/058610 | 8/2002 |
| WO | WO 03/018134 A2 | 3/2003 |
| WO | WO 03/082340 | 10/2003 |
| WO | WO 03/094894 A1 | 11/2003 |
| WO | WO 2004/010941 A2 | 2/2004 |
| WO | WO 2004/039326 A2 | 5/2004 |
| WO | WO 2005/020894 A2 | 3/2005 |
| WO | WO 2005/061004 | 7/2005 |
| WO | WO 2005/063205 | 7/2005 |
| WO | WO 2005/112942 | 12/2005 |
| WO | WO 2005/117832 A1 | 12/2005 |

OTHER PUBLICATIONS

Aasadi M, Salas AP, Motamedi B. Mesoplasty: a new approach to non-surgical liposculpture. Plastic Surgery 2004, Oct. 10, 2004, Philadelphia, PA.

ASAPS. American Society for Aesthetic Plastic Surgery. Lipoplasty (liposuction) without surgery?, Oct. 2002.

Bates B. 'Fat dissolving' substance injects CCs of controversy. Skin and Allergy News 2003, 34.

Banerjee P, Joo JB, Buse JT, Dawson G. Differential solubilization of lipids along with membrane proteins by different classes of detergents. Chem Phys Lipids 1995, 77:65-78.

Bauman LS. Phosphatidylcholine. Skin and Allergy News 2003, 34.

Bellman B. Phosphatidylcholine reaction. Skin and Allergy News 2003, 34.

Bryant, R., Controversial mesotherapy: could it be the next botox. Dermatology Times, Dec. 2004, 1-2.

Buko V, Lukivskaya O, Nikitin V, Tarasov Y, Zavodnick L, Borodinsky A, Gorenshtein B, Janz B, Gundermann K-J, Schumacher R. Hepatic and pancreatic effects of polyenoylphosphatidylcholine in rats with alloxan-induced diabetes. Cell Biochem Function 14:131-7, 1996.

Canty D, Zeisel S, Jolitz A. Lecithin and choline: research update on health and nutrition. Fort Wayne, IN: Central Soya Company, Inc., 1996.

Chalmers K. Fat loss a needle away. http://surgerynews.net/news/0204/meso020402.htm, Feb. 1, 2004.

Durr M, Hager J, Lohr JP. Investigation on mixed micelle and liposome preparations for parental use on soya phosphatidylcholine. Eur J Pharm Biopharm 1994, 40:147-56.

Ebihara L, Hall JE, MacDonald RC, McIntosh TJ, Simon SA. Effect of benzyl alcohol on lipid bilayers. A comparisons of bilayer systems. Biophys J 1979, 28:185-96.

Engelke M, Jessel R, Wiechmann A, Diehl HA. Effect of inhalation anaesthetics on the phase behaviour, permeability and order of phosphatidylcholine bilayers. Biophys Chem 1997, 67:127-38.

Goldman L, Bennet JC, Cecil RL. Cecil Textbook of Medicine. St. Louis, MO: W.B. Saunders Co., 2001.

Gordon LM, Sauerheber RD, Esgate JA, Dipple I, Marchmont RJ, Houslay MD. The increase in bilayer fluidity of rat liver plasma membranes achieved by the local anesthetic benzyl alcohol affects the activity of intrinsic membrane enzymes. J Biol Chem 1980, 255:4519-27.

Gustafson C, Tagesson C. Influence of organic solvent mixtures on biological membranes. Br J Ind Med 1985, 42:591-5.

Hammad MA, Muller BW. Increasing drug solubility by means of bile salt-phosphatidylcholine-based mixed micelles. Eur J Pharm Biopharm 1998, 46:361-7.

Heerklotz H, Seelig J. Correlation of membrane/water partition coefficients of detergents with the critical micelle concentration. Biophys J 2000, 78:2435-40.

Hexsel D., Serra M, Mazzuco R, Dal'Forno T, Zechmeister D. Phosphatidylcholine in the treatment of localized fat. J. Drugs Dermatol 2:511-518, 2003.

Jones MN. Surfactants in membrane solubilisation. Int J Pharm 1999, 177:137-59.

Landman B. Beyond Botox. http://newyorkmetro.com/nymetro/health/bestdoctors/cosmeticsurgery/2003/n_9281/index.html.

Learn about lecithins. Oxford, CT: American Lecithin Company, 2003.

Lester DS, Baumann D. Action of organic solvents on protein kinase C. Eur J Pharmacol 1991, 206:301-8.

Lichtenberg D, Zilberman Y, Greenzaid P, Zamir S. Structural and kinetic studies on the solubilization of lecithin by sodium deoxycholate. Biochemistry 1979, 18:3517-25.

Lichtenberg D, Robson RJ, Dennis EA. Solubilization of phospholipids by detergents. Structural and kinetic aspects. Biochim Biophys Acta 1983, 737:285-304.

Lichtenberg D. Characterization of the solubilization of lipid bilayers by surfactants. Biochim Biophys Acta 1985, 821:470-8.

Lieber CS, Robins SJ, Li J, DeCarli LM, Mak KM, Fasulo JM, Leo MA. Phosphatidylcholine protects against fibrosis and cirrhosis in the baboon. Gastroenterology 106:152-9, 1994.

Lipostabil. Rhone-Polenc Rorer. Cologne, West Germany: Natterman International GMBH, 1990.

Moy, LS. Phosphatidylcholine injections: a study measuring decreased subcutaneous fat thickness. Combined Annual Meeting of the American Society for Dermatologic Surgery and the American Society of Mohs Micrographic Surgery and Cutaneous Oncology, San Diego, CA Sep. 30-Oct. 3, 2004.

Parnham MJ, Wendel A. Phospholipids and liposomes—safety for cosmetical and pharmaceutical use. Nattermann Phospholipid GMBH Scientific Publication No. 2 1995.

Rittes PG. The use of phosphatidylcholine for correction of lower lid bulging due to prominent fat pads. Dermatol Surg 2001, 27:391-2.

Rittes PG. The use of phosphatidylcholine for correction of localized fat deposits. Aesthetic Plast Surg 2003, 27:315-8.

Rosenbaum, M., An exploratory investigation of the morphology and biochemistry of cellulite, Annual Meeting of American Society for Aesthetic Surgery, New York, May 1997, 1934-39.

Rossi ABR, Vergnanini AL. Cellulite: a review. JEADV 14:251-62, 2000.

Rotunda A, Suzuki H, Moy RL, Kolodney MS. Detergent effects of sodium deoxycholate are a major feature of injectable phosphatidylcholine. American Society for Dermatologic Surgery, New Orleans, LA, Oct. 11, 2003.

Rotunda, AM, Suzuki H, Moy RL, Kolodney MS. Detergent effects of sodium deoxycholate are a major feature of an injectable phosphatidylcholine formulation used for localized fat dissolution. Dermatol Surg 30:1001-1008, 2004.

Sager S. New fat removal technique getting raves: Is it safe? Does it work? http://abclocal.go.com/wabc/news/wabc_020703_mesotherapy.html, Feb. 7, 2003.

Schuck S, Honsho M, Ekroos K, Shevchenko A, Simons K. Resistance of cell membranes to different detergents. Proc Natl Acad Sci 2003, 100:5795-800.

Sergio, M. Traitment mesotherapique das xanthelasmas a la phophatidilcoline polyinsaturee.

Serra M., Subcutaneous infiltration with phosphatidylcholine solution for treatment of buffalo hump and fatty pads. 3$^{rd}$ Int'l workshop on adverse drug reactions and lipodystrophy in HIV, Athens, Oct. 2001, 115.

Singer SJ, Nicolson GL. The fluid mosaic model of the structure of cell membranes. Science 1972, 175:720-31.

Teelmann K, Schlappi B, Schupbach M, Kistler A. Preclinical safety evaluation of intravenously administered mixed micelles. Arzneimittelforschung 1984, 34:1517-23.

Toyama M. Next-Gen Liposuction. http://www.time.com/time/europe/forecast2003/html/liposuction.html, Dec. 8, 2002.

Victor S. Phosphatidylcholine works. Skin and Allergy News 2003, 34.

Womack MD, Kendall DA, MacDonald RC. Detergent effects on enzyme activity and solubilization of lipid bilayer membranes. Biochim Biophys Acta 1983, 733:210-5.

Young, VL. Lipostabil: The effect of phosphatidylcholine on subcutaneous fat. Aesthetic Surg J 23:413-417, 2003.

"Love handles can be shrunk without surgery" http://www.macleans.ca/topstories/health/article.jsp?content=20040225_090843_4800, Feb. 25, 2004.

"Lose those love handles" A CBS HealthWatch Special Report http://cbsnewyork.com/healthwatch/local_story_329141707.html, Nov. 25, 2002.

"Health Alert: Lipostabil" http://kyw.com/health/local_story_336152706.html, Dec. 2, 2002.

Powell, A. A. et al. Bile acid hydrophobicity is correlated with induction of apoptosis and/or growth arrest in HCT116 cells. Biochem. J. 2001; 356:481-486.

Rotunda, A.M. et al. Lipomas treated with subcutaneous deoxycholate injections. *J. Am. Acad. Dermatol.* 2005; 53(6): 973-978.

Duncan et al., (2005) "Lipodissolve for Subcutaneous Fat Reduction and Skin Retraction," *Aesthetic Surgery Journal* 25(5):530-543.

* cited by examiner

FIG. 5a
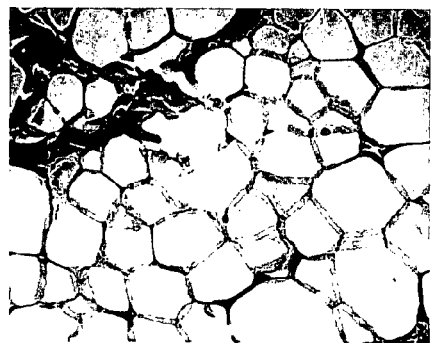
FIG. 5b
FIG. 5c
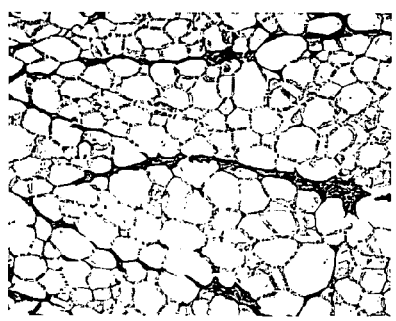
FIG. 5d
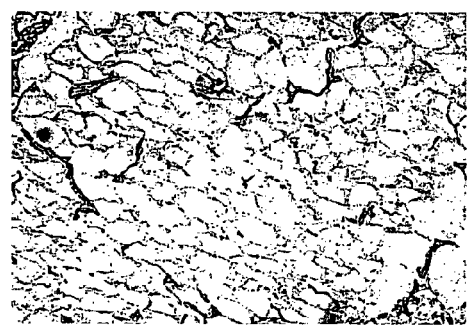
FIG. 5e
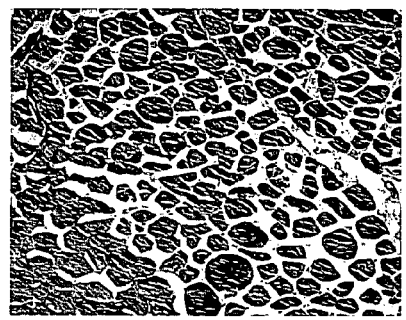
FIG. 5f
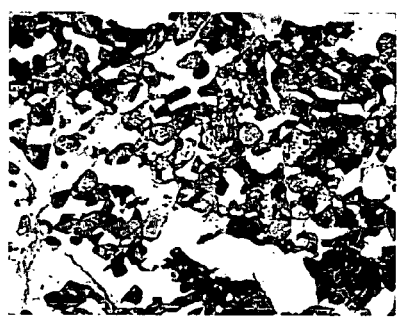
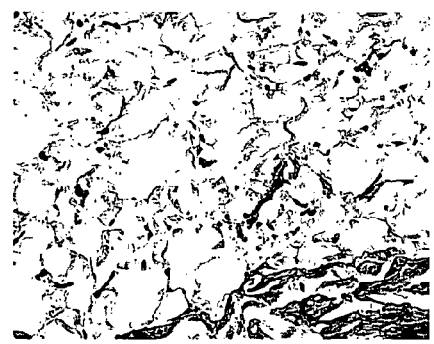
FIG. 5g

METHODS AND COMPOSITIONS FOR THE NON-SURGICAL REMOVAL OF FAT

RELATED APPLICATIONS

The present application claims priority to U.S. Provisional Application Ser. No. 60/572,879 filed May 19, 2004.

FIELD OF THE INVENTION

The present invention is related to compositions and methods useful for the non-surgical removal of localized fat accumulation. Specifically, the present invention is related to pharmacologically active detergent compositions than are suitable for injection directly into a treatment site of a patient in need of fat removal without the need for surgical intervention.

BACKGROUND OF THE INVENTION

Numbers appearing in parentheses at the end of a sentence refer to specific references cited at the conclusion of this specification immediately before the claims.

Formulations containing phosphatidylcholine and bile salts (phosphatidylcholine bile salt formulations, PBF) are increasingly being utilized to treat localized fat accumulation (1-8). Several open label clinical studies have reported promising results using injections of PBFs for the treatment of localized fat accumulation, including lower eyelid fat herniation and "buffalo hump" lipodystrophy (1-3).

Phosphatidylcholine is a natural phospholipid that is an essential component of cell membranes and is important for normal cellular membrane composition and repair. Phosphatidylcholine is also the major delivery form of the essential nutrient choline. Choline itself is a precursor in the synthesis of the neurotransmitter acetylcholine, the methyl donor betaine and phospholipids, including phosphatidylcholine and sphingomyelin among others. Phosphatidylcholine is also involved in the hepatic export of very-low-density lipoproteins.

Bile salts have been used to improve the aqueous solubility of phosphatidylcholine and more recently, medications like amphotericin B, Taxol®, and diazepam (9-14). Highly purified phosphatidylcholine can be combined with the secondary bile salt sodium deoxycholate, an anti-microbial, benzyl alcohol, and water to form a stable, mixed micelle preparation that can be rapidly sterilized and used for intravenous administration (12). Pharmaceutical preparations of this mixture, known as Essentiale® and Lipostabil®, are marketed in other countries for treatment of liver disease and hyperlipidemia, respectively (12, 15).

Rittes first reported that injections of a PBF into subcutaneous fat reduced infraorbital fat herniation (1). Since then, physicians have been using the pharmaceutical preparations or similar, compounded PBFs, to treat lower eyelid fat herniation, as well as fat deposits on the thighs, abdomen, upper back, chin, and arms (2, 3, 5). These PBFs often lack the dl-alpha-tocopherol (vitamin E), B-vitamins, and adenosine monophosphate variably found in Essentiale® and Lipostabil® (2, 16).

Phosphatidylcholine formulations are associated with localized burning sensations, erythema, transient urticaria and variable degrees of pruritus all of which usually resolve within a few days. More serious sequelae of ulceration and pain have also been seen. An infectious granulomatous reaction has been reported in the thigh of a patient at the site of multiple phosphatidylcholine injections (7). Increased dosages of injected phosphatidylcholine have paralleled side effects seen with large doses of oral and intravenous formulations of Lipostabil® and include nausea, diarrhea, abdominal pain and syncope.

The mechanism whereby phosphatidylcholine-containing formulation cause reduction of subcutaneous fat deposits is unknown but several mechanisms have been proposed (4). The first is that phosphatidylcholine could reduce the size of lipocytes by stimulating lipase activity. Alternatively, the PBFs have been postulated to function as a detergent that emulsifies lipocyte cell membranes. Detergents have been used in medicine for decades, specifically, as sclerosing agents commonly used in sclerotherapy (American College of Phlebology, 2003). Detergents possess unique polar and non-polar chemical properties which facilitates emulsification of insoluble substances by reducing surface tension at their interface (17). In fact, laboratory detergents like Triton® X-100 and Empigen® BB are commonly used to disrupt the lipid bilayer of cell membranes (10, 18-21). Two major components of the PBFs, phosphatidylcholine and sodium deoxycholate, have these unique chemical properties and therefore have been used independently as detergents or emulsifying agents (9, 18, 20-25).

Surgical and non-surgical procedures for improving appearance have increased in prevalence as populations age and gain weight. Liposuction is one of the most popular cosmetic surgery procedures and involves the surgical removal of fat deposits using suction and optionally assisted by solutions to assist in fat removal. Liposuction, also known as lipoplasty or suction lipectomy, is a surgical procedure that removes fat through an incision in the skin through which a cannula is inserted. The cannula is connected to a suction source and the unwanted fat is aspirated through the cannula and discarded. Liposuction is performed under general or local anesthesia, depending on the amount and location of the fat to be removed.

The most commonly used forms of liposuction additionally use fluid injection methodologies wherein a medicated solution containing a mixture of salts, an anesthetic and a vasoconstrictor, is infused into the treatment site prior to aspiration of the fat tissue. The medicated solution helps the fat be removed more easily, reduces blood loss and provides anesthesia both during and after surgery.

In an example of adjuvant solutions for liposuction, a United States patent filed on Apr. 22, 1997 and issued as U.S. Pat. No. 5,891,083 on Apr. 6, 1999 by Capella and Capella teaches liposuction and a carrier solution containing a compound for an improved surgical procedure for removing subcutaneous fat. In one embodiment the Capella patent discloses the compound is an enzyme, particularly lipase or colipase. The enzyme is added to a carrier such as saline solution to provide a lipolysis solution. In another embodiment of the invention, Capella teaches emulsifying agents such as bile salts may also be beneficial in combination or as the primary active compound added to the solution. In every embodiment of the Capella invention, the lipolysis solution is administered for a period of time before liposuction to allow for the solution to infiltrate the fat tissue. Nowhere in Capella is the use of a lipolysis solution alone disclosed as a non-surgical means for removing fat from the body. In all examples and specific embodiments disclosed in Capella, liposuction is used as a surgical procedure for fat removal and lipase and bile salts are provided as an adjuvant to liposuction.

However, liposuction and other surgical methods of fat removal are associated with significant adverse events including temporary bruising, swelling, numbness, soreness and burning sensation, risk of infection, pigmentation changes; the formation of fat clots or blood clots which can migrate to the lungs and cause death, excessive fluid loss, which can lead to shock or fluid accumulation that must be drained, friction burns or other damage to the skin or nerves or perforation injury to the vital organs. Additionally, liposuction requires a recovery time of one to two weeks wherein the patient cannot work or perform certain daily activities. Moreover, because surgical procedures such as liposuction require local and occasionally general anesthesia, significant anesthesia-related risks are associated with surgical fat removal.

Therefore it would be desirable to have a method of removing localized fat accumulations that does not require surgery or prolonged recovery time and has fewer adverse side effects than currently available methods.

SUMMARY OF THE INVENTION

The present invention provides a method for the non-surgical removal of localized fat deposits in patients by administration of fat-solubilizing concentrations of phosphatidylcholine-free detergent compositions in pharmaceutically acceptable formulations. Prior to the discovery of the present invention, prior art formulations (hereinafter referred to as phosphatidylcholine bile salt formulations (PBFs)), containing phosphatidylcholine (PC) and bile salts used to reduce localized fat deposits were thought to function through the activity of phosphatidylcholine alone. Detergents such as bile salts were merely added in small quantities to disperse the PC. However, the present invention unexpectedly demonstrates that bile salts alone are the active agents responsible for the reduction of localized fat deposits, and possess detergent effects on muscle and connective tissue.

For the purposes of the present invention, a non-surgical method of fat removal does not include liposuction, llipoplasty or suction lipectomy.

In one embodiment of the present invention, a medical composition for the non-surgical removal of localized fat deposits in a patient is provided which comprises at least one pharmacologically active detergent, optionally at least one pharmaceutically acceptable excipient and optionally at least one additional active ingredient wherein the medical composition does not include phosphotidylcholine. The pharmacologically active detergent can be an ionic detergent, a non-ionic detergent or a zwitterionic detergent.

In one embodiment of the present invention the ionic detergent is at least one pharmacologically active bile salt. The bile salt can be at least one of deoxycholic, cholic, chenodeoxycholic, 7-alpha-dehydroxylate, chenodeoxycholic, litho-cholic, ursodeoxycholic, dihydroxy- and trihydroxy-bile salts. The bile salts can be in the taurine or glycine conjugate forms.

In an embodiment of the present invention, the pharmacologically active detergent can be a non-ionic detergent such as alkylaryl polyether alcohol. In another embodiment of the present invention, the pharmacologically active detergent can be zwitterionic detergent such as lauryldimethylbetaine.

In yet another embodiment of the present invention the medical composition contains one or more additional active ingredients. One or more additional active ingredients can include anti-inflammatory agents such as a steroidal anti-inflammatory agent or a non-steroidal anti-inflammatory agent; analgesics and dispersion agents such as hyaluronidase or collagenase.

In another embodiment of the present invention, the medical composition contains pharmaceutically acceptable excipients.

In an embodiment of the present invention, the patient is a human.

In another embodiment of the present invention, a method is provided for the non-surgical removal of localized fat deposits in a patient having localized fat accumulation comprising administering a fat solubilizing amount of a pharmacologically active detergent composition, wherein the non-surgical method does not include liposuction.

In an embodiment of the present invention, the pharmacologically active detergent composition contains at least one pharmacologically active detergent, optionally at least one pharmaceutically acceptable excipient and optionally at least one additional active ingredient, and wherein the pharmacologically active detergent composition does not contain phosphatidylcholine.

In embodiments of the present invention, the pharmacologically active detergent composition is administered by subcutaneous injection directly into fat tissue.

In an embodiment of the present invention, the localized fat accumulation is lower eyelid fat herniation, lipomas, lipodystrophy, buffalo hump lipodystrophy or fat deposits associated with cellulite.

In another embodiment of the present invention, a medical composition is provided for removing localized accumulation of fat in a patient with lower eyelid fat herniation comprising a fat solubilizing amount of deoxycholic acid, and the medical composition does not contain phosphatidylcholine.

In an embodiment of the present invention a non-liposuction method for the non-surgical removal of localized fat deposits in a patient is provided comprising the non-surgical administration of a pharmacologically active detergent composition consisting essentially of at least one pharmacologically active detergent, optionally at least one pharmaceutically acceptable excipient and optionally at least one additional active ingredient, and the medical composition does not include phosphatidylcholine.

BRIEF DESCRIPTION OF THE DRAWINGS

FIG. 5 depicts light microscopy of porcine skin biopsies after treatment with compositions made according to the teachings of the present invention revealing (a) control lipocytes and (b) lipocytes after PBF injection (H&E, original magnification, ×20); (c) control lipocytes and (d) lipocytes after injection of sodium deoxycholate alone (H&E, original magnification, ×10); (e) control muscle and (f) muscle after injection of phosphatidylcholine alone (H&E, original magnification, ×10); (g) fat after injection with Empigen® detergent (H&E, original magnification, ×20).

DETAILED DESCRIPTION OF THE INVENTION

The present invention addresses the problem of localized fat accumulation in patients by providing a non-surgical method for removing fat deposits by administration of fat-solubilizing concentrations of detergents in pharmaceutically acceptable formulations.

Injections using prior art formulas (phosphatidylcholine bile formulation, PBF) that combine purified phosphatidylcholine (PC) and sodium deoxycholate, a bile salt used for phospholipid solubilization, have been used to treat infraorbital fat herniation and other areas of localized fat accumulation (1-8). Based on phosphatidylcholine's role as an emulsifier in bile and its use in the treatment of hyperlipidemia, phosphatidylcholine has been postulated as the active ingredient in PBFs (1, 2, 21, 25-27). The detergents such as bile salts in these prior art compositions were added merely to disperse or solubilize the presumed active ingredient, PC. However, to date, there are no published reports supporting this theory. The present inventors have unexpectedly demonstrated that the bile salt was actually the active agent for localized fat emulsification.

Among detergents, bile salts are particularly potent solubilizers of lipid bilayer membranes (9, 20, 21, 23, 28). All biologic cell membranes are composed of the same bilipid structure, and are therefore subject to solubilization by detergents (10, 19, 34). Solubilization of cell membranes by a detergent involves distribution of the detergent between lipid bilayers, destabilization of the bilayer, disintegration, and subsequent formation of mixed micelles (composed of detergent and cell membrane lipid) (10, 19, 21). Bile salts, and other detergents, decrease surface tension at the border of immiscible materials and allows the breakdown of large aggregates into smaller and smaller particles. In tissue, these agents dissolve cell membranes and cause cell lysis. An inflammatory response is generated, causing the body to remove the detergent solubilized material.

Figure 2A:
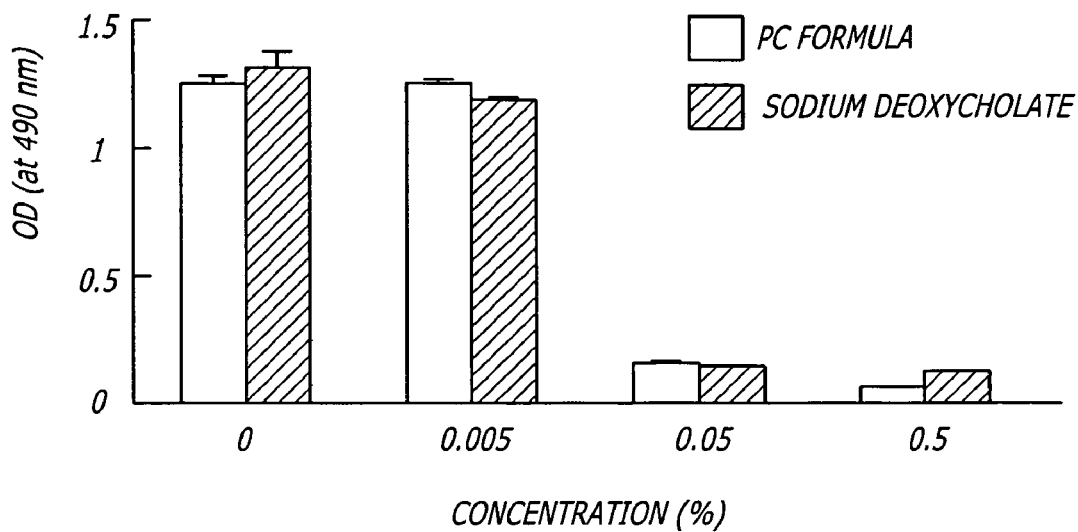
FIG. 2 depicts the effects of phosphatidylcholine bile formulation (PC Formula, PBF) and sodium deoxycholate alone on cultured cell viability according to the teachings of the present invention: (a) MTS assay measuring viability of keratinocytes exposed to the PC Formula and sodium deoxycholate alone; (b) Lactate dehydrogenase (LDH) assay measuring LDH release by cells exposed to the PC Formula and sodium deoxycholate alone.

For this reason, the present inventors compared sodium deoxycholate with the complete PBF using a simple, quantitative assay measuring cell viability (FIG. 2a). It is not possible to isolate and test pure phosphatidylcholine because it is insoluble in aqueous solutions unless it is combined with substances like bile salts (12). Phosphatidylcholine is highly soluble in ethanol, methanol, chloroform, and other organic solvents, yet these agents can damage lipid bilayers (29-31). In preliminary experiments, there was no difference in cell lysis and histology between pure, isolated PC and the ethanol used to dissolve it. Although benzyl alcohol, one of the components of the PC formula, has been shown to affect the fluidity of cell membranes, it is a not a detergent, and therefore, its limited quantity in the formula has negligible lytic effects on cell membranes (32, 33).

Because penetration into intact tissues may be likely a limiting factor, cell cultures were used to determine the dilutions of the reagents (PBF and deoxycholate) necessary to affect cells. Deoxycholate profoundly decreased the viability of cultured cells approximately equal to the complete PBF (FIG. 2a). This finding was reproduced in tissue by exposing porcine fat to PBF and deoxycholate (FIG. 3). These results support the unexpected observation that sodium deoxycholate plays a major, active role in the PBF.

Figure 2B:
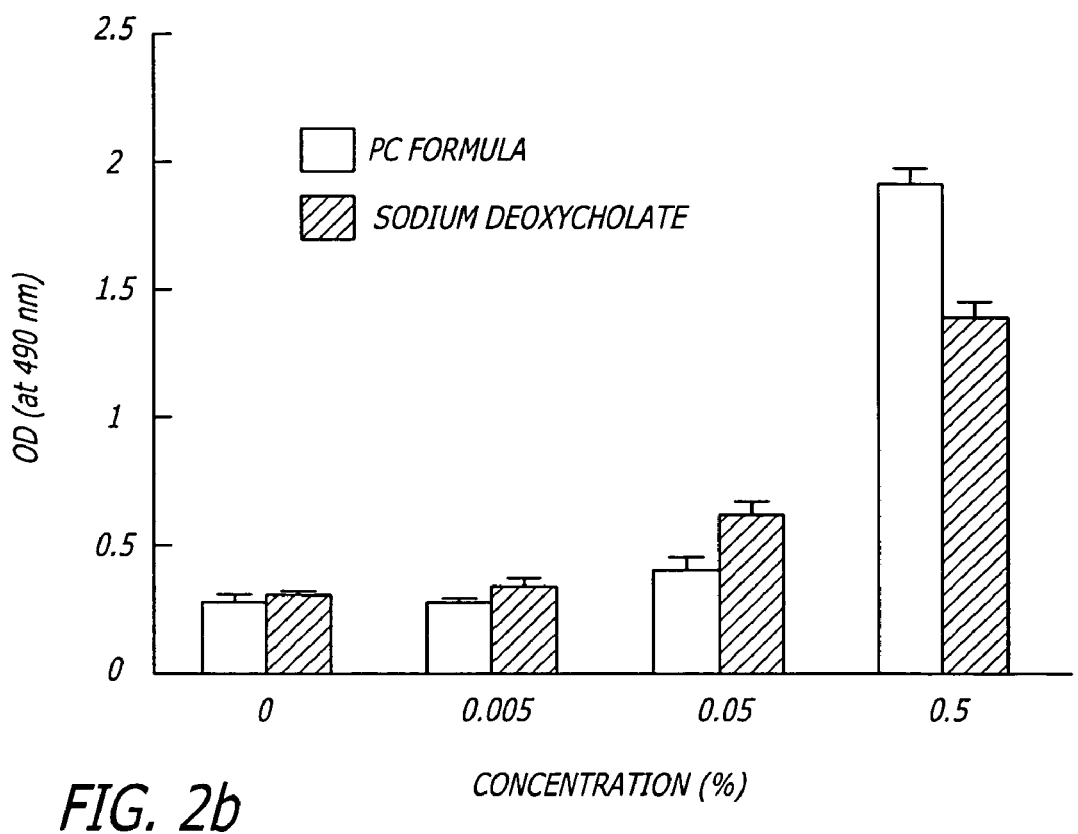
Figure 4:
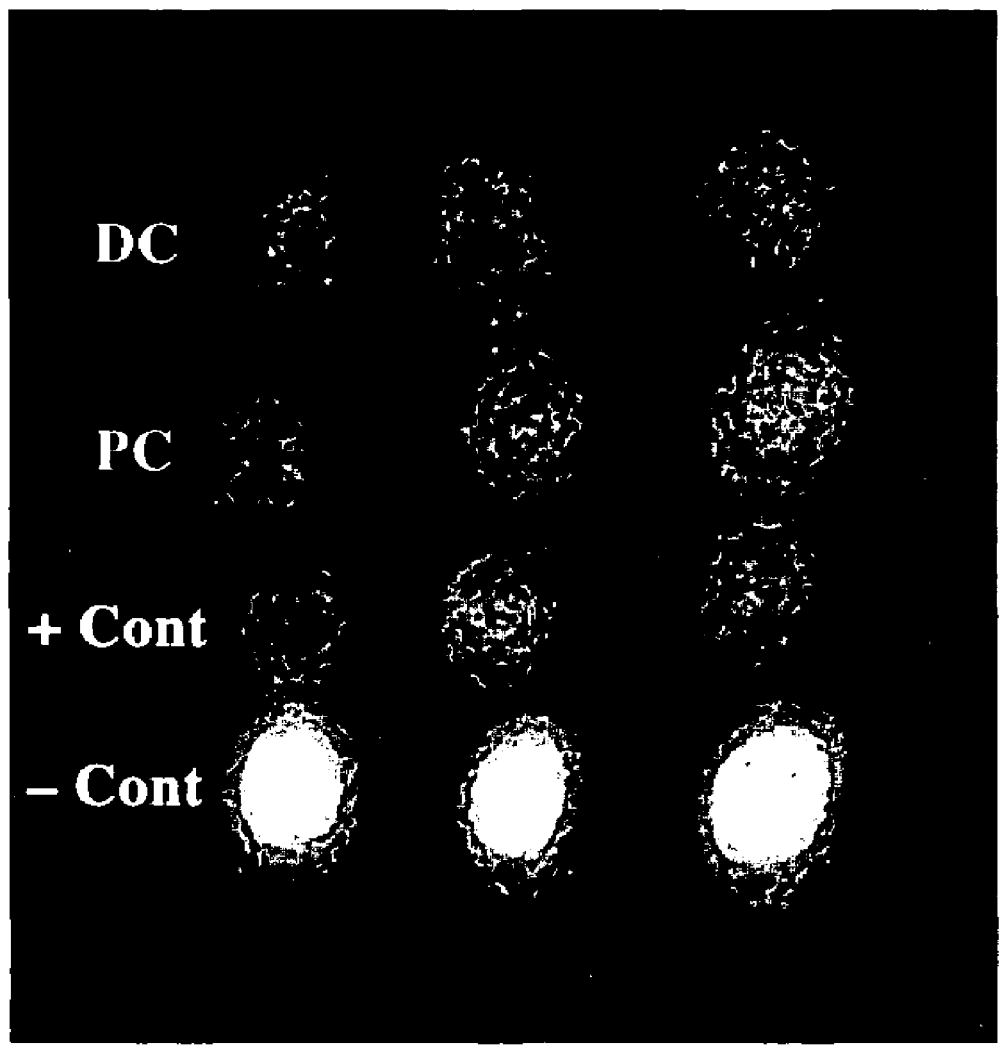
FIG. 4 depicts calcein fluorescence in fat specimens treated with sodium deoxycholate alone (DC), PBF (PC), Triton® detergent as positive control (+Cont), and PBS buffer as negative control (−Cont) according to the teachings of the present invention.

A non-binding hypothesis of the present inventors was that deoxycholate and PBF affect cell viability by disrupting cell membranes through detergent action. Membrane lysis in cultured cells was measured using a lactate dehydrogenase (LDH) assay and within tissue using calcein, a fluorescent marker retained in cells with intact cell membranes. The LDH assay measures the activity of LDH, which is a cytosolic enzyme released when cells are lysed. Both the PBF- and deoxycholate-treated cell cultures demonstrated a concentration-dependent increase in cell lysis (FIG. 2b). Moreover, the direct lytic effects observed in cultured cells treated with these agents suggest activity independent of endogenous lipase. Calcein was lost in the fat specimens exposed to the PBF, deoxycholate, and Triton® X-100, a known laboratory detergent (FIG. 4). This finding confirmed that disruption of cell membranes occurs in fresh tissue exposed to both the PBF and deoxycholate.

Comparing the effects of the PBF to deoxycholate in cell culture led to the surprising result that deoxycholate caused similar loss of cell viability, but less cell lysis. These differences may be concentration dependent or there may be synergistic effects between phosphatidylcholine and deoxycholate within the formula. Nonetheless, the data demonstrate that, at concentrations similar to those used clinically, deoxycholate and the PBF had similar effects on tissue histology and cell viability. Taken together, these data unexpectedly demonstrate that deoxycholate acts as the active component in the prior art PBF.

In order to illustrate the effect of detergents on tissue histology, fresh porcine skin was injected with PBF, deoxycholate, and well-characterized laboratory detergents (FIG. 5). All reagents caused significant disruption of lipocyte organization compared to PBS injection (control). These results were similarly observed within muscle and connective tissue. Rapid dissolution of cell borders by the test substances and the similarity of their effects to well characterized detergents substantiate that the PBF and deoxycholate function as detergents. The limitation with this experimental model is that it does not reveal the true sequelae that occur after injection into living tissue. It is apparent from clinical reports that a brisk inflammatory response, evident as erythema and edema, occurs after injection (1-3). Repeated inflammation can potentially lead to fibrosis, especially after multiple injections. Fibrosis has been reported in several patients who developed firm nodules at injection sites after PBF administration that eventually resolve over several months (35).

Histologic findings reveal that the injectable PBF and deoxycholate alone cause architectural disruption in fat and muscle, but had no apparent affect on the epidermis, dermis, or adnexae (FIG. 5). However, Empigen® BB, a potent laboratory detergent, had profound histologic effects on dermal collagen (connective tissue). Alternatively, fat and muscle can be more sensitive to detergent treatment than these other structures at the tested concentrations (similar to those used in clinical practice).

Through a series of laboratory experiments utilizing fresh tissue specimens and cell cultures, the present inventors have demonstrated that the prior art PBF popularly used in subcutaneous injections for fat dissolution works primarily by causing non-specific lysis of cell membranes. Cell membrane are constituents of all tissue types; specifically, the present inventor demonstrated that these detergents cause solubilization of fat, muscle and connective tissue. Therefore the present inventors concluded that sodium deoxycholate, the bile salt component of the formula used to dissolve the phosphatidylcholine, was the major active ingredient of these prior art formulations. This conclusion is supported by the fact that bile salts are potent solubilizers of cell membranes. Moreover, the mechanism of the PBF and sodium deoxycholate in fat dissolution is likely detergent action.

In an embodiment of the present invention, a medical composition of biologically compatible detergents includes pharmacologically active detergents and pharmaceutically acceptable excipients in an aqueous vehicle.

Therefore it is within the scope of the present invention that detergents other than bile salts can be used to dissolve fat according to the teachings of the present invention. Biologically compatible detergents that can be used in embodiments of the present invention include, but are not limited to, ionic detergents, non-ionic detergents, zwitterionic detergents and bile salts. Non-limiting examples of bile salts include deoxycholic, cholic, chenodeoxycholic, 7-alpha-dehydroxylate, chenodeoxycholic, lithocholic, ursodeoxycholic, dihydroxy- and trihydroxy-bile acids and the corresponding salts, taurine or glycine conjugates and related detergents. A non-limiting example of an ionic detergent useful in an embodiment of the present invention is sodium deoxycholate. A non-limiting example of a non-ionic detergent useful in an embodiment of the present invention is alkylaryl polyether alcohol (Triton® X-100). A non-limiting example of a zwitterionic detergent useful in an embodiment of the present invention is lauryldimethylbetaine (Empigen® BB). Suitable concentrations of detergents for use according to the teachings of the present invention range from approximately 0.001% to approximately 50.000%. It is understood that the final concentration is dependent on many factors known to persons skilled in the art including, but not limited to, location and size of the treatment site.

Compositions produced according to the present invention can include other active ingredients including, without limitation, and in any compatible combination, anti-inflammatory agents, analgesics, dispersion agents, penetration enhancers and pharmaceutically acceptable excipients.

Anti-inflammatory agents suitable for use with the compositions of the present invention can include both steroidal anti-inflammatory agents and non-steroidal anti-inflammatory agents. Suitable steroidal anti-inflammatory agent can include, although are not limited to, corticosteroids such as hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone and the balance of its esters, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and mixtures thereof can be used.

A second class of anti-inflammatory agents which is useful in the compositions of the present invention includes the nonsteroidal anti-inflammatory agents. The variety of compounds encompassed by this group are well-known to those skilled in the art.

Suitable non-steroidal anti-inflammatory agents useful in the compositions of the present invention include, but are not limited to: the oxicams, such as piroxicam, isoxicam, tonexicam, sudoxicam, and CP-14,304; the salicylates, such as salicylic acid, aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepiract, clidanac, oxepinac, and felbinac; the fenamates, such as mefenamic, meclofenamic, flufenamic, niflumic, and tolfenamic acids; the propionic acid derivates, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and the pyrazoles, such as phenybutazone, oxyphenbutazone, feprazone, azapropazone, and trimethazone. Mixtures of these non-steroidal anti-inflammatory agents can also be employed, as well as the pharmaceutically-acceptable salts and esters of these agents.

Analgesics suitable for use with the pharmacologically active detergent composition of the present invention to reduce discomfort due to inflammation after subcutaneous injection of the formulation of the present invention include, but are not limited to, injectable local amine and ester anesthetics. Non-limiting examples of analgesics include lidocaine, mepivacaine, bupivacaine, procaine, chloroprocaine, etidocaine, prilocalne and tetracaine. Mixtures of these analgesics can also be employed, as well as the pharmaceutically acceptable salts and esters or these agents.

Pharmacologically acceptable aqueous vehicles for the compositions of the present invention can include, for example, any liquid solution that is capable of dissolving a detergent and is not toxic to the particular individual receiving the formulation. Examples of pharmaceutically acceptable aqueous vehicles include, without limitation, saline, water and acetic acid. Typically, pharmaceutically acceptable aqueous vehicles are sterile.

Pharmacologically active detergent compositions useful in embodiments of the present invention are formulated for the non-surgical removal of localized fat deposits. As used herein, "non-surgical" refers to medical procedures that do not require an incision. Injections are examples of non-surgical procedures. Liposuction is a surgical procedure.

In one embodiment of the present invention, the pharmacologically active detergent composition is administered by injection, for example, by bolus injection. In order to be effective, the detergent composition must have direct contact with the fat tissue regardless of how it is infused. The detergent formulations can be injected subcutaneously or infused directly into the fat. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents such as suspending, stabilizing and/or dispersing agents.

A "pharmaceutically acceptable excipient" means a compound that is useful in preparing a pharmaceutical composition that is generally safe, non-toxic and neither biologically nor otherwise undesirable, and includes excipients that are acceptable for veterinary use or human pharmaceutical use. A pharmaceutically acceptable excipient as used in the specification and claims includes both one and more than one such excipient. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, phosphatidylcholine, cellulose, sterile water, syrup, and methyl cellulose. The formulations can additionally include: lubricating agents such as talc, magnesium stearate, and mineral oil; wetting agents; emulsifying and suspending agents; and preserving agents such as methyl- and propylhydroxy-benzoates and benzyl alcohol. The compositions of the present invention can be formulated so as to provide quick, sustained or delayed release of the active ingredient after administration to the patient by employing procedures known in the art.

Additional excipients suitable for formulation with the detergent compositions of the present invention include penetration enhancers and dispersion agents. Non-limiting examples of dispersion agents which allow the dispersion of drugs in tissue include hyaluronidase and collagenase. Hyaluronidase functions to augment tissue permeability and spread or dispersion of other drugs. Collagenase has been used to isolate adipocytes from subcutaneous fat and does not have lytic effects on adipocytes themselves. Additionally hyaluronidase and collagenase can facilitate healing by accelerating removal of necrotic tissue after treatment with the detergent formulations of the present invention.

The pharmacologically active detergent compositions of the present invention are useful for treating localized fat accumulations, including but not limited to lower eyelid fat herniation, accumulations on the waist, hips and other cosmetic areas, xanthelasma, lipomas and lipodistrophy, including "buffalo hump" lipodystrophy (3). In another embodiment, the detergent compositions of the present invention is useful for treating fat deposits associated with cellulite.

The following examples are provided to more precisely define and enable the compositions and methods of the present invention. It is understood that there are numerous other embodiments and methods of using the present invention that will be apparent embodiments to those of ordinary skill in the art after having read and understood this specification and examples. The following examples are meant to illustrate one or more embodiments of the invention and are not meant to limit the invention to that which is described below.

EXAMPLES

Example 1

Sodium Deoxycholate and Phosphatidylcholine Formulations

Phosphatidylcholine bile salt formulation (PBF) (5.0% highly purified soy derived PC, 4.75% sodium deoxycholate, and 0.9% benzyl alcohol, in sterile water, Table 1) was obtained from Hopewell Pharmacy, Hopewell, N.J. Sodium deoxycholate and Triton® X-100 detergent (Triton®, alkylaryl polyether alcohol) were obtained from Sigma-Aldrich Corp. (St. Louis, Mo.). Empigen® BB detergent (Empigen®, lauryldimethylbetaine, Calbiochem, Biosciences, Inc., La Jolla, Calif.). Stock reagents (5% dilutions) were prepared in PBS buffer.

Figure 1:
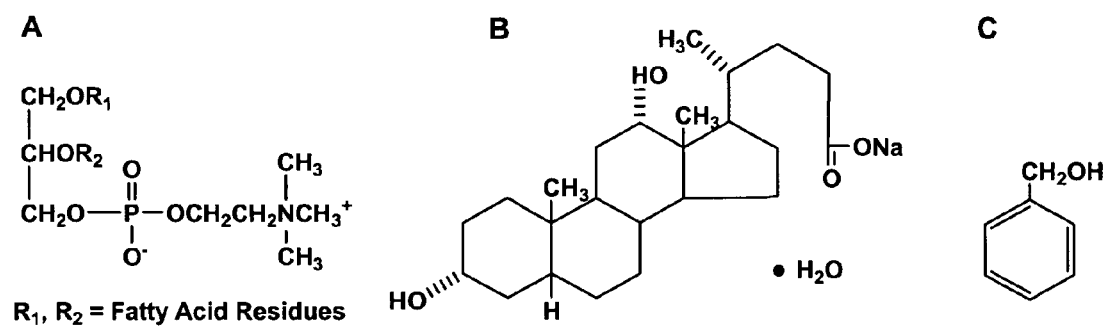
FIG. 1 depicts the molecular structure of (a) phosphatidylcholine (b) sodium deoxycholate and (c) benzyl alcohol.

The molecular structure of (a) phosphatidylcholine, (b) sodium deoxycholate and (c) benzyl alcohol are depicted in FIG. 1.

TABLE 1

| Injectable PBF | |
|---|---|
| Phosphatidylcholine | 5.00% (w/v) |
| Sodium deoxycholate | 4.75% |
| Benzyl alcohol | 0.90% |
| Water | 100 mL |

Example 2

Effects of Sodium Deoxycholate and Phosphatidylcholine Solutions in Cultured Cells To measure cell viability after detergent treatment, HaCaT human keratinocyte cells were cultured in DMEM (Dulbecco's modified Eagle's medium) supplemented with 10% fetal calf serum, penicillin, and streptomycin. HaCaT cells were cultured in 6 well plates and incubated with 0%, 0.005%, 0.050% or 0.500% PBF (PC Formula) or sodium deoxycholate for 30 min at 37° C. prior to determination of cell viability using the MTS assay, which uses a tetrazolium compound that produces a color change when bioreduced by metabolically active cells (CellTiter 96® AQ$_{ueous}$ Non-Radioactive Cell Proliferation Assay, Promega, Corp. Madison, Wis.). Cell viability was determined by an absorbance spectrophotometer (at 490 nm) after a 4 hour incubation with the assay at 37° C. To determine cell viability in fresh tissue, fat specimens were incubated for 4 hours in 24 well plates with stock reagents and the MTS assay. Tissue specimens were then visualized for color change and the amount of MTS in their supernatants was measured by absorbance (at 490 nm). All studies were performed in triplicate. Absorbance at 490 nm (OD 490) is proportional to the number of living cells in the culture. There was comparable OD 490 in the control and 0.005% dilutions of both compounds (FIG. 2a), indicating little effect of these substances on cell viability at this concentration. Cell viability progressively decreased at 0.05% and 0.5% concentrations of both solutions.

Cell lysis in response to detergent treatment was determined in HaCaT cells incubated with the reagents at the indicated cell dilutions for 30 min at 37° C. Lactate dehydrogenase release was measured by absorbance (at 490 nm) after a 1 hour incubation with the LDH assay as recommended by the manufacturer (CytoTox 96® Non-Radioactive Cytotoxicity Assay, Promega). All studies were performed in triplicate. LDH release is directly proportional to absorbance at 490 nm (OD 490). There was minimal LDH release from control cells and those incubated with 0.005% dilutions of both compounds (FIG. 2b). There was progressively more LDH released at 0.05% and 0.5% of the PBF and deoxycholate.

Example 3

Effects of Sodium Deoxycholate and Phosphatidylcholine Solutions in Porcine Tissue Porcine tissue was obtained immediately after sacrifice, shaved, and placed on ice for a maximum of four hours before use. Fat specimens were obtained by removing the epidermis and dermis of a punch biopsy with a scalpel and trimmed. Fat specimens were loaded with calcein dye by incubating 1 hour at 37° C. with Calcein-AM (Sigma). Stock reagents were added to the fat specimens and incubated for 30 min at 37° C. with gentle agitation. Calcein retention was determined by tissue fluorescence using purple (411 nm) light and visually observing the emitted green (500 nm) light using an emission filters.

Histology was performed by injecting stock reagent solutions (0.5 mL) into full thickness porcine skin at various levels (epidermis, dermis, and subcutaneous tissue) with 1.0 mL syringes and 30-gauge, 0.5 inch needles. Needle depth was visualized along the margin of the porcine tissue with the intent of saturating the target tissue. One hour after incubation with PBS at 37° C., multiple 5.0 mm biopsy specimens were obtained from the injected sites, each condition performed in triplicate. Tissue was fixed in formaldehyde, paraffin-embedded, and stained with hematoxylin-eosin. Specimens were evaluated by a board-certified dermatopathologist who was blinded to the treatment protocol.

Figure 3A:
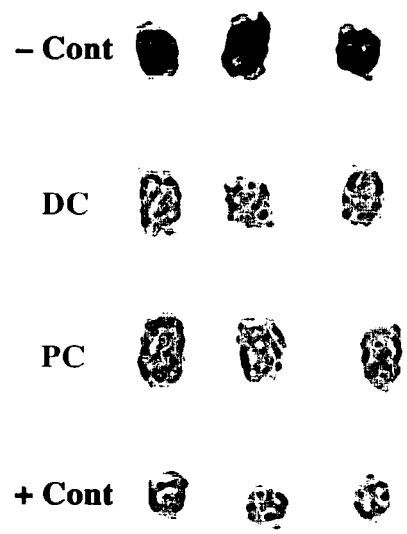
FIG. 3 depicts the effects of PBF and sodium deoxycholate alone on primary porcine fat tissue according to the teachings of the present invention: (a) MTS assay producing purple pigment, indicating living cells, in fat specimens treated with the PBS buffer as negative control (−Cont), sodium deoxycholate alone (DC), the PBF (PC), and Triton® detergent as positive control (+Cont); (b) A comparison of fat cell viability between the different treatments.
Figure 3B:
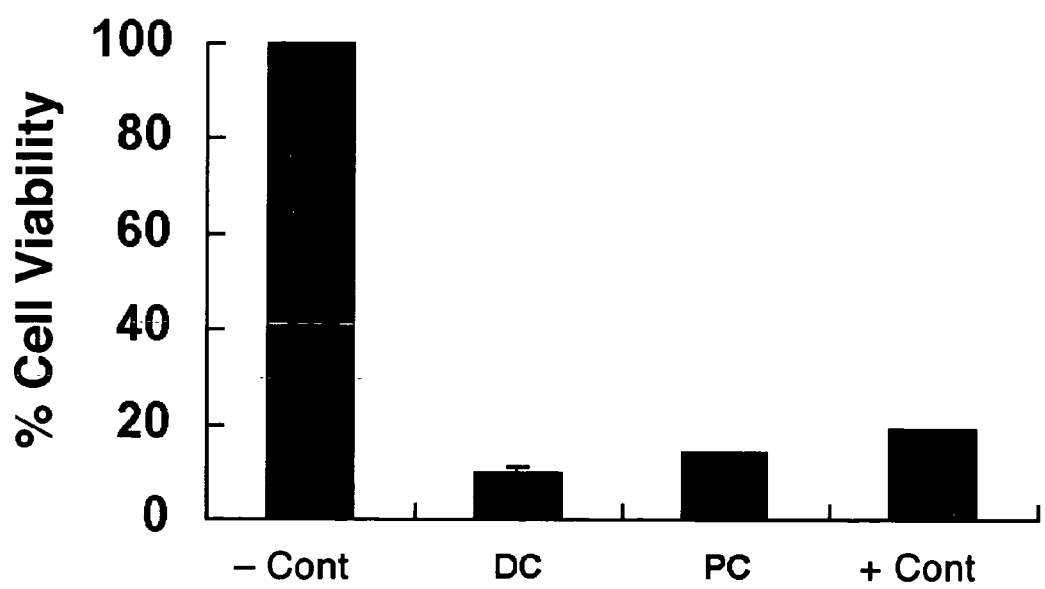

Fresh porcine skin was used to determine if the effects of these detergent substances on cultured cells were similar in tissue. FIG. 3a demonstrates the production of dark purple pigment (indicating viable cells) in fat tissue treated with the PBS buffer (negative control) using the MTS assay. The PBF and 5% solutions of deoxycholate and Triton® detergent (positive control) demonstrated a comparable loss of purple dye (indicating cell death) in the treated fat specimens. The difference in fat cell viability between the solutions was quantified by measuring the absorbance (at 490) of the supernatants collected from the treated fat specimens (FIG. 3b). All reagents had significant effects on the fat cell viability of fresh tissue.

Cell lysis was confirmed using a calcein dye release assay. Calcein becomes fluorescent after hydrolysis and is retained in cells that have intact cell membranes. Because it does not label dead cells and is lost under conditions that cause cell lysis, loss of green fluorescence in fat tissue samples loaded with the dye calcein indicates cell lysis (FIG. 4). Samples treated with the deoxycholate, PBF, and Triton® detergent (positive control) exhibited similar loss of fluorescence.

The histologic changes resulting from injection of PBF, deoxycholate, and Empigen®, are shown in FIG. 5. Phosphatidylcholine bile salt formulation (FIG. 5b) and deoxycholate (FIG. 5d) produced histologic effects similar to those caused by Empigen® (FIG. 5g) and Triton® (not shown), two well-characterized laboratory detergents. These changes were apparent in both fat and muscle. Marked blurring and dissolution of adipocyte cell membranes with disruption of its normal lobular architecture were seen after injection of both the PBF (FIG. 5b) and deoxycholate (FIG. 5d). FIG. 5f demonstrates muscle fiber disarray and atrophy after PBF injection. Similar changes in muscle tissue were visible in the specimens treated with deoxycholate and the Triton® and Empigen® detergents. There were no changes in the epidermis, dermis, or adnexal structures after injection of the reagents with the exception of Empigen®, which caused loss of fibroblast nuclear staining and hyalinization of dermal collagen.

Example 4

Clinical Experience with Sodium Deoxycholate Compositions

Figure 6A:
FIG. 6 depicts a lipoma removed from a patient two days after injection with deoxycholate according to the teachings of the present invention: (a) gross pathology and (b) histology (H&E, original magnification, ×20).
Figure 6B:
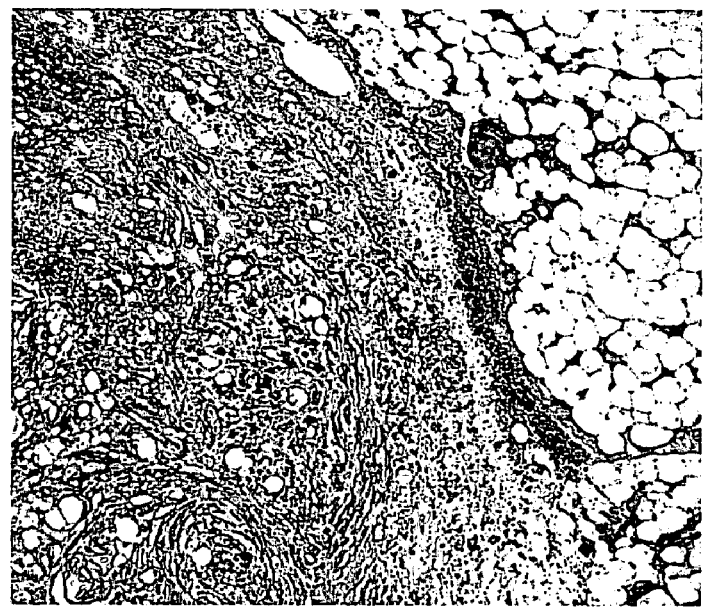

Patients having lipomas, benign, isolated collections of adipose tissue, were injected with sodium deoxycholate (DC) solutions without phosphatidylcholine directly into the lipoma. The results of this study demonstrate that the detergent effects of deoxycholate seen on fat in animal tissues are reproducible clinically in humans. All injected lipomas were reduced in size after at least one treatment with varied concentrations of deoxycholate (Table 2). A lipoma from one patient, injected with 1% DC, was excised after treatment and pathological and histological analysis performed. Within the excised lipoma, necrosis is visible grossly (FIG. 6a) with a well demarcated area of hemorrhage and necrosis on the lateral edge extending into the middle of the lipoma fat which contrasts with the normal lipoma fat which is lighter in color. Histological analysis (FIG. 6b) reveals a well defined area of hemorrhage and necrotic fat as well as a significant inflammatory reaction which contrasts to the adjacent normal round clear fat cells.

TABLE 2

Reduction in size of lipomas after DC treatment

| Lipoma | Size (cm) Pre-treatment | Size (cm) Post-treatment | Total Treatments (% DC injected) |
| --- | --- | --- | --- |
| 1 | 2.00 × 1.00 | 1.25 × 0.50 | 2 (2.5%) |
| 2 | 2.00 | 1.50 × 0.50 | 3 (5% and 2.5%) |
| 3 | 2.00 × 2.50 | 2.00 × 1.00 | 3 (5% and 2.5%) |
| 4 | 4.00 × 3.50 | 2.50 × 2.00 | 2 (1%) |
| 5 | 2.00 × 1.75 | 1.25 | 2 (1%) |
| 6 | 2.80 | 0.50 | 1 (5%) |
| 7 | 1.00 | Imperceptible | 1 (1%) |

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

REFERENCES

1. Rittes P G. The use of phosphatidylcholine for correction of lower lid bulging due to prominent fat pads. Dermatol Surg 2001, 27:391-2.
2. Ablon G, Rotunda A M. Treatment of lower eyelid fat pads using phosphatidylcholine: clinical trial and review. Derm Surgery 2004, 30:422-7.
3. Serra M. Subcutaneous infiltration with phosphatidylcholine solution for treatment of buffalo hump and fatty pads. Antiviral Therapy 2001, 6:75-6.
4. ASAPS. American Society for Aesthetic Plastic Surgery. Lipoplasty (liposuction) without surgery?, October, 2002.
5. Bauman L S. Phosphatidylcholine. Skin and Allergy News 2003, 34.
6. Bates B. 'Fat dissolving' substance injects CCs of controversy. Skin and Allergy News 2003, 34.
7. Bellman B. Phosphatidylcholine reaction. Skin and Allergy News 2003, 34.
8. Victor S. Phosphatidylcholine works. Skin and Allergy News 2003, 34.
9. Lichtenberg D, Zilberman Y, Greenzaid P, Zamir S. Structural and kinetic studies on the solubilization of lecithin by sodium deoxycholate. Biochemistry 1979, 18:3517-25.
10. Lichtenberg D, Robson R J, Dennis E A. Solubilization of phospholipids by detergents. Structural and kinetic aspects. Biochim Biophys Acta 1983, 737:285-304.
11. Teelmann K, Schlappi B, Schupbach M, Kistler A. Preclinical safety evaluation of intravenously administered mixed micelles. Arzneimittelforschung 1984, 34:1517-23.
12. Durr M, Hager J, Lohr J P. Investigation on mixed micelle and liposome preparations for parental use on soya phosphatidylcholine. Eur J Pharm Biopharm 1994, 40:147-56.
13. Alkan-Onyuksel H, Ramakrishnan S, Chai H B, Pezzuto J M. A mixed micellar formulation suitable for the parenteral administration of taxol. Pharm Res 1994, 11:206-12.
14. Hammad M A, Muller B W. Increasing drug solubility by means of bile salt-phosphatidylcholine-based mixed micelles. Eur J Pharm Biopharm 1998, 46:361-7.
15. Parnham M J, Wendel A. Phospholipids and liposomes—safety for cosmetical and pharmaceutical use. Nattermann Phospholipid GMBH Scientific Publication No. 2 1995.
16. Lipostabil. Product insert: Aventis Pharma, 2003.
17. Goldman L, Bennet J C, Cecil R L. Cecil Textbook of Medicine. St. Louis, Mo.: W.B. Saunders Co., 2001.
18. Womack M D, Kendall D A, MacDonald R C. Detergent effects on enzyme activity and solubilization of lipid bilayer membranes. Biochim Biophys Acta 1983, 733:210-5.
19. Lichtenberg D. Characterization of the solubilization of lipid bilayers by surfactants. Biochim Biophys Acta 1985, 821:470-8.
20. Banerjee P, Joo J B, Buse J T, Dawson G. Differential solubilization of lipids along with membrane proteins by different classes of detergents. Chem Phys Lipids 1995, 77:65-78.
21. Almgren M. Mixed micelles and other structures in the solubilization of bilayer lipid membranes by surfactants. Biochim Biophys Acta 2000, 1508:146-63.
22. Schuck S, Honsho M, Ekroos K, Shevchenko A, Simons K. Resistance of cell membranes to different detergents. Proc Natl Acad Sci 2003, 100:5795-800.
23. Heerklotz H, Seelig J. Correlation of membrane/water partition coefficients of detergents with the critical micelle concentration. Biophys J 2000, 78:2435-40.
24. Learn about lecithins. Oxford, Conn.: American Lecithin Company, 2003.
25. Canty D, Zeisel S, Jolitz A. Lecithin and choline: research update on health and nutrition. Fort Wayne, Ind.: Central Soya Company, Inc., 1996.
26. Feldman M, Scharschmidt B F, Sleisenger M H, Fordtran J S, Zorab R. Sleisenger & Fordtran's Gastrointestinal and Liver Disease. New York: Saunders, 2002.
27. Lipostabil. Rhone-Polenc Rorer. Cologne, West Germany: Natterman International GMBH, 1990.
28. Jones M N. Surfactants in membrane solubilisation. Int J Pharm 1999, 177:137-59.
29. Gustafson C, Tagesson C. Influence of organic solvent mixtures on biological membranes. Br J Ind Med 1985, 42:591-5.
30. Lester D S, Baumann D. Action of organic solvents on protein kinase C. Eur J Pharmacol 1991, 206:301-8.
31. Engelke M, Jessel R, Wiechmann A, Diehl H A. Effect of inhalation anaesthetics on the phase behaviour, permeability and order of phosphatidylcholine bilayers. Biophys Chem 1997, 67:127-38.

32. Ebihara L, Hall J E, MacDonald R C, McIntosh T J, Simon S A. Effect of benzyl alcohol on lipid bilayers. A comparisons of bilayer systems. Biophys J 1979, 28:185-96.
33. Gordon L M, Sauerheber R D, Esgate J A, Dipple I, Marchmont R J, Houslay M D. The increase in bilayer fluidity of rat liver plasma membranes achieved by the local anesthetic benzyl alcohol affects the activity of intrinsic membrane enzymes. J Biol Chem 1980, 255:4519-27.
34. Singer S J, Nicolson G L. The fluid mosaic model of the structure of cell membranes. Science 1972, 175:720-31.
35. Rittes P G. The use of phosphatidylcholine for correction of localized fat deposits. Aesthetic Plast Surg 2003, 27:315-8.

We claim:

1. A method for non-surgical removal of a localized fat deposit in a patient having such a deposit and desiring to remove such a deposit, wherein the deposit is contacted with a composition consisting essentially of an effective amount of up to 5% deoxycholic acid or salt thereof and an excipient wherein said deoxycholic acid or salt thereof is a sole fat removing component and wherein the composition does not include phosphatidylcholine.

2. The method of claim 1 wherein said salt is the sodium salt of deoxycholic acid.

* * * * *

UNITED STATES PATENT AND TRADEMARK OFFICE
CERTIFICATE OF CORRECTION

| | |
|---|---|
| PATENT NO. | : 7,622,130 B2 |
| APPLICATION NO. | : 11/054171 |
| DATED | : November 24, 2009 |
| INVENTOR(S) | : Michael S. Kolodney et al. |

Page 1 of 1

It is certified that error appears in the above-identified patent and that said Letters Patent is hereby corrected as shown below:

TITLE PAGE:

Item (74) Attorney, Agent or Firm, please add -- K&L Gates, LLP; Paul Tran --.

IN THE SPECIFICATION:

In Column 8, Line 31, please replace the term "prilocalne" with -- prilocaine --.

Signed and Sealed this

Sixteenth Day of February, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,622,130 B2 | Page 1 of 1 |
| APPLICATION NO. | : 11/054171 | |
| DATED | : November 24, 2009 | |
| INVENTOR(S) | : Kolodney et al. | |

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 958 days Delete the phrase "by 958 days" and insert -- by 1035 days --

Signed and Sealed this

Thirty-first Day of August, 2010

David J. Kappos
*Director of the United States Patent and Trademark Office*